United States Patent
Thiele et al.

(10) Patent No.: US 10,512,444 B2
(45) Date of Patent: Dec. 24, 2019

(54) ULTRASONIC COLOR FLOW MAP FOR ANALYSIS OF MITRAL REGURGITATION

(71) Applicant: KONINKLIJKE PHILIPS N.V., Eindhoven (NL)

(72) Inventors: Karl Erhard Thiele, Andover, MA (US); Qifeng Wei, Wayland, MA (US); Mona Shrestha, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 200 days.

(21) Appl. No.: 14/407,095

(22) PCT Filed: Jun. 17, 2013

(86) PCT No.: PCT/IB2013/054964
§ 371 (c)(1),
(2) Date: Dec. 11, 2014

(87) PCT Pub. No.: WO2014/001955
PCT Pub. Date: Jan. 3, 2014

(65) Prior Publication Data
US 2015/0148679 A1    May 28, 2015

Related U.S. Application Data

(60) Provisional application No. 61/665,046, filed on Jun. 27, 2012.

(51) Int. Cl.
*A61B 8/06* (2006.01)
*A61B 8/08* (2006.01)
(Continued)

(52) U.S. Cl.
CPC ............ *A61B 8/065* (2013.01); *A61B 8/0883* (2013.01); *A61B 8/461* (2013.01); *A61B 8/486* (2013.01);
(Continued)

(58) Field of Classification Search
CPC ....... A61B 8/065; A61B 8/0883; A61B 8/461; A61B 8/466; A61B 8/486; A61B 8/488;
(Continued)

(56) References Cited

U.S. PATENT DOCUMENTS 5,285,788 A * 2/1994 Arenson ................. A61B 8/06
600/441
5,373,847 A * 12/1994 Cape ....................... A61B 8/06
600/455
(Continued)

FOREIGN PATENT DOCUMENTS

| | | |
|---|---|---|
| CN | 101001574 A | 7/2007 |
| DE | 202008003245 U1 | 10/2008 |
| WO | 9621215 | 7/1996 |

*Primary Examiner* — Katherine L Fernandez (57) ABSTRACT

An ultrasonic diagnostic imaging system is described which assesses regurgitant flow through a mitral valve by color-flow imaging. A Doppler processor produces Doppler velocity measurements of blood flow around a regurgitant valve to identify an iso-velocity surface to be used in the PISA method of regurgitant flow quantification. The velocity measurements are used to color pixels in the colorflow image and are mapped to a plurality of colors for a color bar used with the image. The color bar exhibits distinct color transitions at one or more velocities in the velocity range of the color bar which distinctively identify an iso-velocity surface in the colorflow image. The color bar may be formed with an aliasing velocity in the middle of the bar, between a zero velocity reference color of the bar and an end of the bar, and the aliasing velocity aligned with a desired iso-velocity and used to create the color transition.

20 Claims, 4 Drawing Sheets

(51) Int. Cl.
  *A61B 8/00*   (2006.01)
  *G01S 15/89*  (2006.01)
  *G01S 7/52*   (2006.01)

(52) U.S. Cl.
  CPC ............ *A61B 8/488* (2013.01); *A61B 8/5207* (2013.01); *A61B 8/5215* (2013.01); *A61B 8/5223* (2013.01); *A61B 8/54* (2013.01); *G01S 7/52071* (2013.01); *G01S 15/8979* (2013.01); *A61B 8/466* (2013.01); *A61B 8/5246* (2013.01); *G01S 7/52073* (2013.01)

(58) Field of Classification Search
  CPC ... A61B 8/5207; A61B 8/5215; A61B 8/5223; A61B 8/5246; A61B 8/54; G01S 15/8979; G01S 7/52071; G01S 7/52073
  See application file for complete search history.

(56) References Cited

U.S. PATENT DOCUMENTS

| | | | |
|---|---|---|---|
| 5,997,479 A | 12/1999 | Savord et al. | |
| 6,013,032 A | 1/2000 | Savord | |
| 6,623,432 B2 | 9/2003 | Powers et al. | |
| 2002/0151794 A1* | 10/2002 | Li | A61B 8/065 600/454 |
| 2008/0097210 A1 | 4/2008 | Salgo et al. | |

* cited by examiner

ULTRASONIC COLOR FLOW MAP FOR ANALYSIS OF MITRAL REGURGITATION

This application is the U.S. National Phase application under 35 U.S.C. § 371 of International Application No. PCT/IB2013/054964, filed on Jun. 17, 2013, which claims the benefit of U.S. Provisional Application No. 61/665046 filed on Jun. 27, 2012. These applications are hereby incorporated by reference herein.

This invention relates to medical diagnostic ultrasound systems and, in particular, to the use of diagnostic ultrasonic imaging systems for the analysis of mitral regurgitation flow.

Regurgitant flow is a serious medical condition which required analysis and appropriate treatment. Just prior to the contraction of the left ventricle to pump blood into the body, the mitral valve must close completely so that the contraction will eject all of the blood flow into the aorta. If the valve does not close completely, some of the blood in the left ventricle will be ejected back into the left atria through the opening in the incompletely sealed valve. This backflow of blood, typically a small, momentary jet of blood flow squirting back through the incompletely closed valve leaflets, reduces the outflow of blood from the heart and hence the efficiency of each heart contraction. The heart must then pump more rapidly in order to supply the body with its necessary supply of nourishing blood flow. The heart is overworked due to its inefficiency, leading to heart failure.

Clinicians have used ultrasonic imaging for many years to try to detect regurgitant blood flow. Ultrasonic detection of valvular regurgitation was initially done by looking for the above-mentioned jet of blood in an ultrasound image of the left side of the heart. During the past twenty years observation of the jet has been facilitated by two dimensional (2D) colorflow Doppler imaging, in which the high speed and turbulence of the small jet of blood is detected by careful search for these abnormal local flow velocities near the leaking heart valve. But acquisition of the image plane in which the jet is most prevalent, coupled with heart and valve motion and blood flow turbulence in the vicinity of the mitral valve, as well as the momentary occurrence of the jet, pose challenges to this subjective approach. In recent years, in cases where the location of the jet can be observed ultrasonically, clinicians have used a technique called PISA, an acronym for Proximal Iso-velocity Surface Area, to try to quantify the regurgitant blood flow. In this method the suspect valve and the region inside the LV heart chamber and proximal to the valve are imaged by colorflow Doppler imaging. At the time of occurrence of the jet a flow convergence region (FCR) is formed in the proximal region as blood flow velocities in the region instantaneously accelerate toward the regurgitant orifice. This flow pattern results in aliasing in the colorflow image as the flow velocities momentarily exceed the velocity range used for the colorflow image. A colorflow image at this moment is captured and frozen on the display screen. A measurement is then made of the velocity v at the first aliasing line of the FCR, and a measurement is made of the distance r from the aliasing line to the presumed center of the valve orifice. These two measurements are then used to compute the flow rate through the orifice using the expression $Q_r = 2 \pi r^2 v$.

An important step in the PISA technique is to discern the iso-velocity surface in the ultrasound image. The surface may be an arcuate curve in a two dimensional ultrasound image or a semi-hemispherical area in a 3D ultrasound image. It is necessary to identify the iso-velocity surface with high precision, since the radial distance measured from the iso-velocity surface to the regurgitant orifice is a squared term in the flow rate equation. One approach used in the past to better discern the iso-velocity surface is to try to use the aliasing threshold of the colorflow system to identify the surface. A colorflow ultrasound system operates by sampling the flow of blood at a sampling rate known as the pulse repetition frequency. This sampling rate will satisfy the Nyquist criterion for blood flow velocities that translate to a frequency of up to one-half the sampling rate. The range of these adequately sampled blood flow velocities is generally displayed alongside the ultrasound image as a color bar of different colors ranging from +V to −V around a velocity of zero, where V is the maximum velocity that is sampled to meet the Nyquist criterion. Thus, the higher the velocity of blood flow to be detected, the greater the Doppler sampling rate must be. If a flow velocity exceeds the +V or −V speed, the Doppler processor will "wrap around" and display a color at the other end of the color bar. The normal practice in blood flow diagnosis is to use a Doppler sampling rate which is high enough so that all expected blood flow velocities will be adequately sampled in accordance with the Nyquist criterion, and will not exceed the velocity at which aliasing sets in.

The non-standard use of the color bar which can be used to better discern the iso-velocity surface is to adjust the color bar in what is known as a "baseline shift." As mentioned above, a velocity of zero is conventionally in the center of the color bar, equally spaced between the maximum velocities of +V and −V. A baseline shift is performed by moving the zero velocity point to an off-center position so that the flow velocity to be used as that of the iso-velocity surface is at one end of the color bar. This will cause aliasing to occur at the intended iso-velocity flow velocity, resulting in a wrap-around of the displayed colors above the iso-velocity flow velocity. When the opposite ends of the color bar have different colors, such as red at one end and blue at the other, the displayed colors will be different on either side of the iso-velocity flow rate. While this use of the color bar will intentionally cause aliasing to occur and renders the color bar inapposite to what is displayed, normally an undesired result, the color difference on either side of the iso-velocity can make the iso-velocity surface easier to discern in the ultrasound image. What is desirable is a color bar specifically designed for mitral regurgitation conditions that highlights the iso-velocity surface in the colorflow image while maintaining the color bar representative of the flow conditions being displayed.

In accordance with the principles of the present invention, an ultrasonic diagnostic imaging system is described for analyzing regurgitant blood flow by color Doppler imaging. A color Doppler image is colored in accordance with a color bar that exhibits a distinctive color change between a central zero velocity reference and an end of the color bar. The velocity at which the color change occurs is in the range of an expected iso-velocity value so that the color transition will distinctively mark an iso-velocity surface in a colorflow image of mitral regurgitation. In a preferred implementation a color change is present both above and below the zero velocity reference level to accommodate either direction of blood flow.

Figure 1:
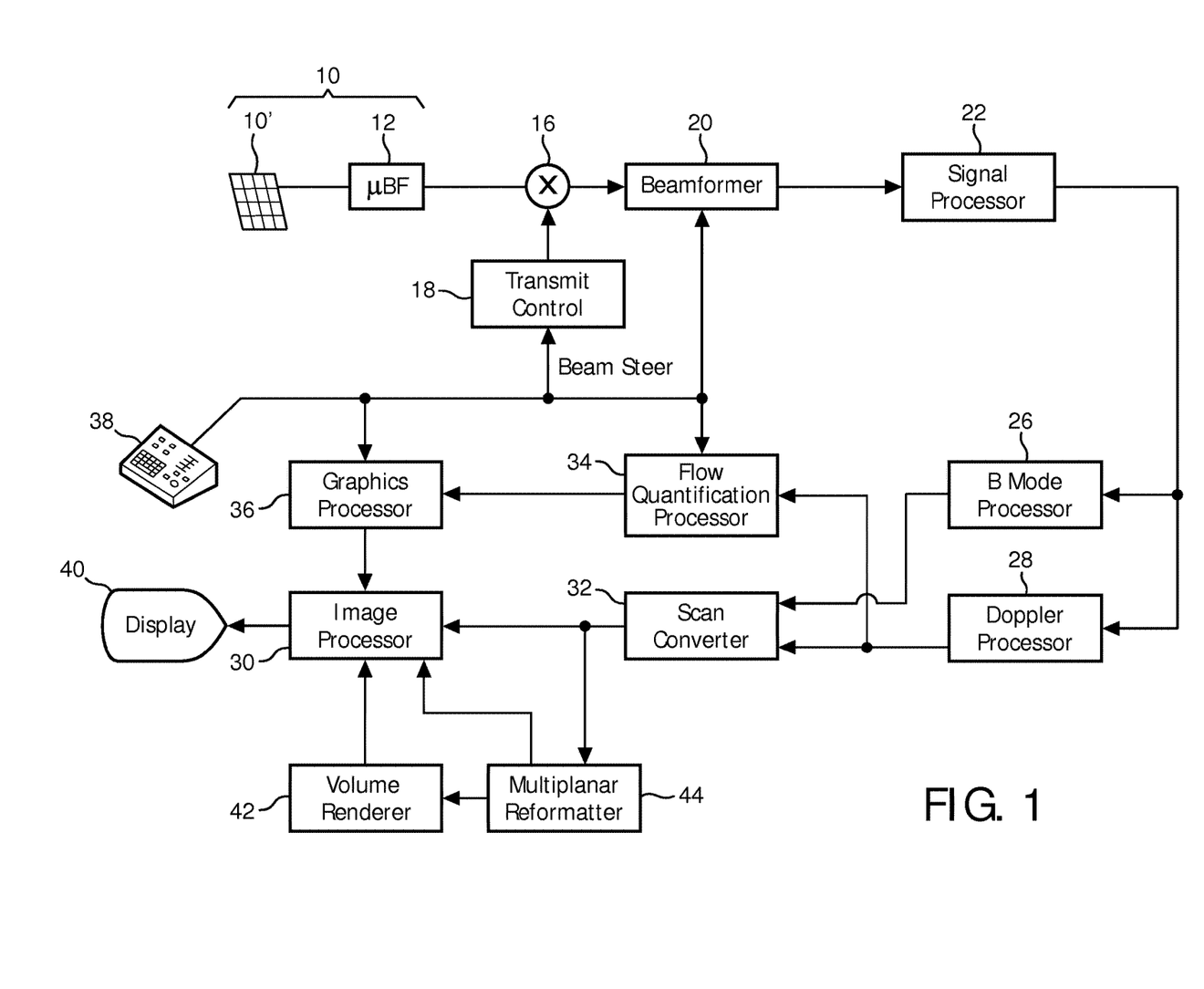
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. In FIG. 1 a transducer array 10' is provided in an ultrasound probe 10 for transmitting ultrasonic waves and receiving echo information. The transducer array 10' is preferably a two dimensional array of transducer elements capable of scanning in three dimensions, for instance, in both elevation and azimuth about the location of the mitral valve, for 3D imaging. The transducer array is coupled to a microbeamformer 12 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 10 under control of the microbeamformer 12 is directed by a transmit controller 18 coupled to the T/R switch and the beamformer 20, which receives input from the user's operation of the user interface or control panel 38. One of the functions controlled by the transmit controller is the direction in which beams are steered. Beams may be steered straight ahead from (orthogonal to) the transducer array, or at different angles for a wider field of view.

The partially beamformed signals produced by the microbeamformer 12 are coupled to a main beamformer 20 where partially beamformed signals from individual patches of transducer elements are combined into a fully beamformed signal. For example, the main beamformer 20 may have 128 channels, each of which receives a partially beamformed signal from a patch of 12 transducer elements. In this way the signals received by over 1500 transducer elements of a two dimensional array can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle reduction, signal compounding, and noise elimination.

The processed signals are coupled to a B mode processor 26 and a Doppler processor 28. The B mode processor 26 employs amplitude detection for the imaging of structures in the body such as the tissue of the heart wall, the mitral valve, and blood cells. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor 28 processes temporally distinct signals from tissue and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. For mitral regurgitation assessment of a rapidly occurring jet, short ensemble lengths (fewer samples) are generally employed so that a high acquisition frame rate can be realized. The rate at which (or time intervals between) signal samples are acquired is known as the pulse repetition frequency (PRF) and establishes the maximum velocity of blood flow which can be measured without aliasing. To satisfy the Nyquist criterion for sampling and prevent aliasing, the blood flow must be sampled in the ensemble at a rate which is at least twice the equivalent frequency of the highest velocity of flow being measured. The Doppler shift •f may be estimated by an equation of the form $$\Delta f = \frac{2vf_0 \cos\theta}{c}$$

where $f_0$ is the transmit frequency, c is the ultrasound propagation speed, v is velocity, and • is the angle between the beam direction and the direction of the blood flow. As the Doppler equation illustrates, there is a direct relation between the Doppler frequency f and flow velocity v. This enables a direct translation of Doppler frequencies to flow velocity values and to colors representing those velocity values.

The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40.

In accordance with the principles of the present invention, blood flow velocity values produced by the Doppler processor 28 are coupled to a flow quantification processor 34. The flow quantification processor operates as described below to produce a measure of the flow rate through a regurgitant orifice, the volume flow through the orifice, and the spatial location of the orifice. The flow quantification processor may receive input from the user control panel 38, such as an initial estimate of the location of the orifice as described below. Output data from the flow quantification processor is coupled to a graphics processor 36 for the reproduction of output data from the processor with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of a display of multiple multiplanar reformatted (MPR) images which may be used to quantify regurgitant flow in the MPR images in accordance with the present invention as described below.

When the user operates the control panel 38 to perform color Doppler (colorflow) imaging, the flow velocities produced by the flow quantification processor are matched by the processor to a range of different colors. These colors are used to color the pixels in the image where motion is occurring with colors corresponding to their flow values such as the velocity of flow. The flow quantification processor also produces an indicator of the colors used and their corresponding range of flow values which is displayed in conjunction with the ultrasound image. Generally this color indicator is shown as a bar of different colors, ranged against the limits of their corresponding velocities, typically the maximum velocity in both directions relative to the probe (positive and negative velocities) and the zero velocity or DC reference value. The graphics processor 36 then causes the color bar to be displayed alongside the colorflow image. The colorflow image is thus a qualitative display of the velocities of blood flow, where the colors indicate whether velocities are relatively high or low and in which direction relative to the probe.

Figure 2:
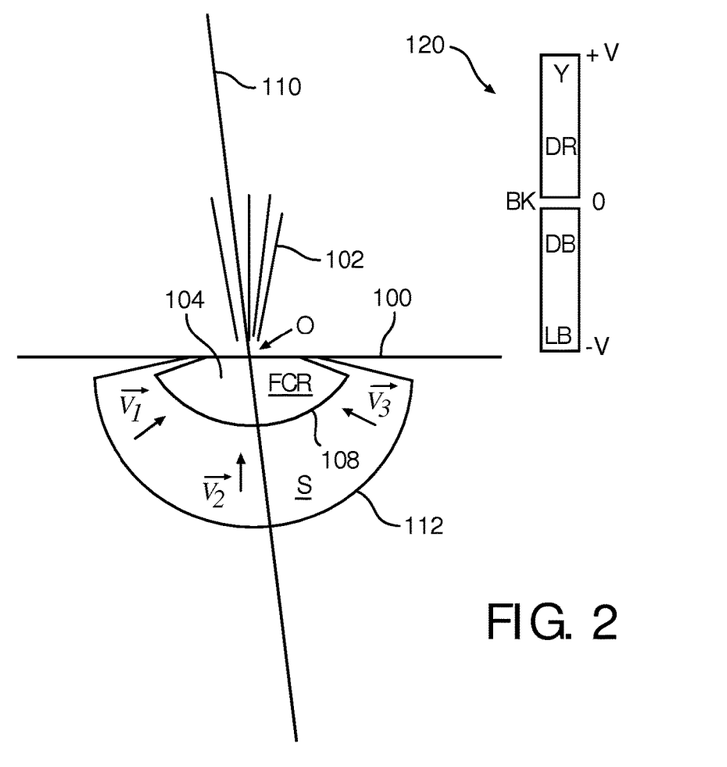
FIG. 2 illustrates an ultrasound color Doppler image of a regurgitant jet.
Figure 3:
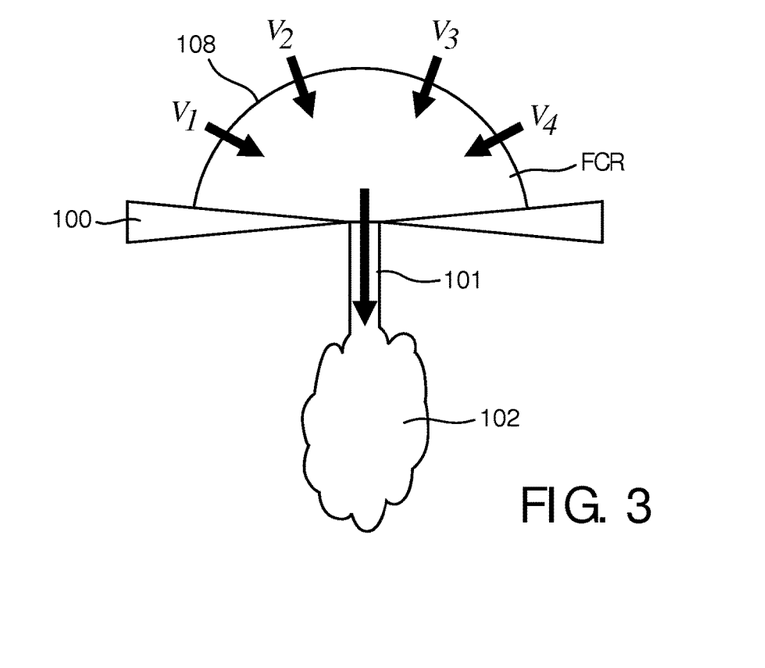
FIG. 3 illustrates a PISA measurement of regurgitant flow.

FIGS. 2 and 3 illustrate mitral regurgitation and the use of the PISA technique to assess the regurgitant flow. The mitral valve is represented at 100 with an orifice O that is not completely closed and leaks when the mitral valve is closed and the left ventricle is contracting to pump blood. This regurgitant flow is back into the chamber of the left atrium which is above the mitral valve plane in FIG. 2 and below it in FIG. 3. The PISA technique is premised on the assumption that the regurgitant flow involves blood in an acceptance zone S within a region bounded by surface 112 that is converging toward the leaking orifice as indicated by flow vectors $V_1$, $V_2$, $V_3$ and $V_4$. The technique is also premised on the assumption that these flow vectors will all exhibit the same velocity at a surface 108 approaching the orifice O, an iso-velocity surface, inside of which is a flow convergence region (FCR) where the blood flow converges to pass through the orifice O. The flow velocity in the outer limits of the acceptance zone is relatively low, but increases in velocity as the blood approaches the orifice and is ejected into the left atrium. The proximal ejection of blood is in a high velocity jet 101 known as the vena-contracta. As the jet extends further into the left atrium it becomes disbursed in a chaotic turbulent flow region 102. The turbulent flow region 102 will appear as a mosaic of different colors due to the diversity of velocities and flow directions in the turbulence. A gauge of these colors is displayed for the clinician in a color bar 120 shown to the right of the colorflow image in FIG. 2. The standard color bar has a central level which is the zero velocity (DC) level 0. As indicated in the drawing, this zero velocity level is typically colored black (BK), since no-flow conditions are not of significant interest in this procedure. Above the zero velocity level is a spectrum of colors ranging in this example from dark red (DR) to bright yellow (Y) to the +V end of the color bar. The +V end is the maximum velocity V for the selected PRF, above which aliasing will occur. The plus sign of +V indicates that the flow direction of these colors is toward the ultrasound probe. The lower half of the color bar is similar, ranging from dark blue (DB) colors to light blue (LB) colors for flow away from the probe. The lower end of the color bar similarly ends at a velocity of −V below which aliasing occurs. This color bar 120 tells the user that blood flow velocities not in excess of a velocity of V will be accurately represented in the image by the colors of the bar.

In FIG. 2, a beam direction 110 indicates the central beam of an ultrasound probe aimed directly at the mitral valve orifice from above or below the mitral valve plane. Since the PISA technique requires the identification of the iso-velocity surface of uniform velocity with considerable precision to make radial measurements from the surface to the orifice, it is desirable for the clinician to be able to quickly and confidently spot the iso-velocity surface 108 in a colorflow image.

Figure 4:
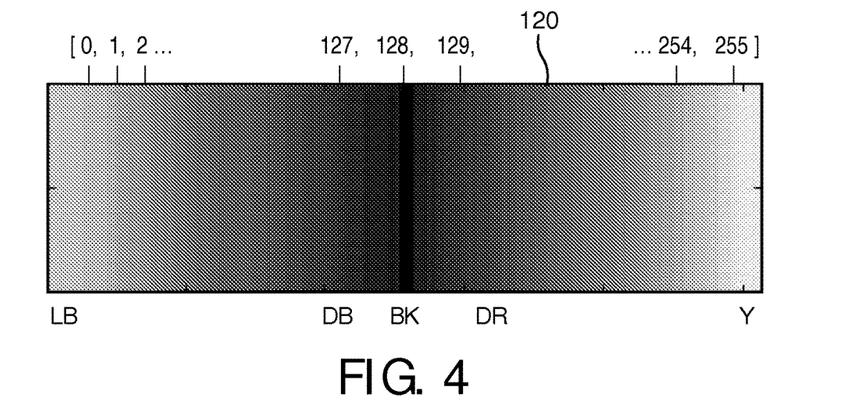
FIG. 4 illustrates the scaling of a conventional color bar for a color Doppler image.

The flow velocity values produced by the flow quantification processor 34 are related to the range of colors in the following way. The velocities measured in both directions are first segmented into a sequence of 256 discrete velocity indices, from the highest negative velocity (−V) to zero velocity to the highest positive velocity (+V). These 256 velocity indices are then mapped to 256 different RGB colors of the color spectrum of the color bar 120 and used correspondingly in the colorflow image. For example, the −V velocity can have an index value of 0, the zero velocity value can have an index value of 128, and the +V velocity can have an index value of 256 in the sequence. FIG. 4 illustrates this range of flow velocities [−V . . . 0 . . . +V] sequenced to discrete index values [0, . . . 128, . . . 256] which are then mapped to the range of colors [LB . . . BK . . . Y]. This discrete sequencing of the velocities means that an index value in the sequence of [0, . . . 128, . . . 256] of a specific image pixel can be applied to a look-up table to look up the corresponding color for the pixel. In this example a −V velocity will have an index value of 0 which looks up a light blue pixel color; a velocity of zero will have an index value of 128 which looks up the black pixel color; and a velocity of +V will have an index value of 256 which looks up a bright yellow pixel color.

Figure 5:
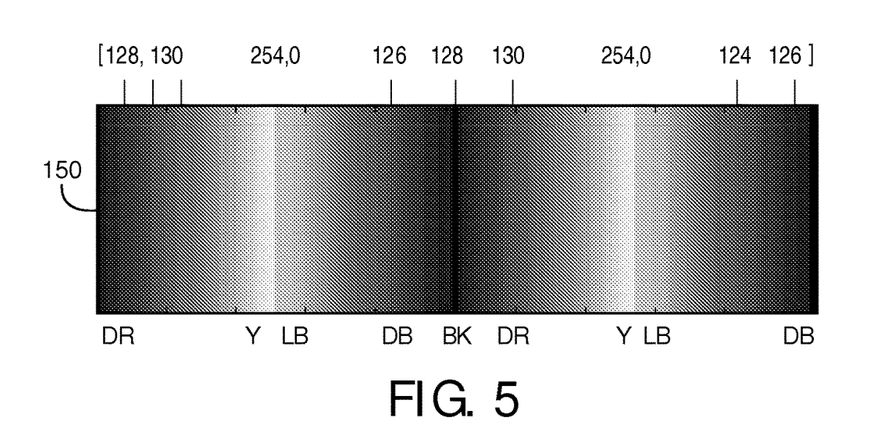
FIG. 5 illustrates a color bar for a color Doppler image configured in accordance with the principles of the present invention.

In accordance with the principles of the present invention, a color bar spectrum of colors is used which exhibits a distinctive color transition at an intermediate velocity between an end of the spectrum and the zero velocity level, an example of which is shown in FIG. 5. In this example the color bar 150 has two such transitions, one above the zero velocity level and its +V end and another below the zero velocity level and its −V end. The example of FIG. 5 also uses the same indexing scheme as used with the color bar of FIG. 4. The [0 . . . 256] index sequence is used twice, once for colors above the zero velocity level and again for colors below. Since the same spectral range of colors is used above and below the zero velocity level, the same color is selected in either instance. The zero velocity index value of 128 will again address the black color, which is again in the middle of the color bar but also at the ends of the bar. This is done so that the distinct color shift from yellow to light blue in between is the most distinctive in the display. In this example the brightest yellow color is selected by index value 256 and the lightest blue color is selected by the immediately adjacent index value of 0. This sequence is also immune to aliasing errors, for if a high positive velocity wraps around it will appear as a high negative velocity; the color changes from bright yellow to light blue, which is the intended change in color.

Use of the color bar of FIG. 5 can be as follows. The clinician sets the colorflow system to sample the blood flow for a maximum velocity equal to the desired velocity at the iso-velocity surface 108. For example, the desired iso-velocity is set to 30 cm. per second. Aliasing will then occur at the desired frequency which occurs at the 256 to 0 or 0 to 256 index point of the color transition. Since this transition occurs in both the upper and lower halves of the color bar, the distinctive color transition will occur regardless of the direction of flow and the placement of the probe, either above or below the mitral valve.

Another implementation which uses a different indexing scheme is for the clinician to set the aliasing velocity at twice the desired iso-velocity. For example, if the desired iso-velocity is 25 cm. per second, the aliasing frequency V is set at ±50 cm. per second. The measured velocities are then sequenced from 0 to 256 in either direction from +V to −V (or −V to +V). The zero velocity level will then fall at an index point of 128 and the color transition levels will then fall at 64 and 192, in the middle of the color bar on either side of the zero velocity level. This implementation does not rely on color aliasing for the distinctive color transitions. In the illustrated example the transition can be from yellow to light blue or from light blue to yellow, depending on the direction of the jet. Either will distinctively indicate the iso-velocity surface.

While the illustrated example of FIG. 5 places the color transition points exactly between the central zero velocity level and each end of the color bar, it is understood that the color transition can be placed above or below the mid-point in each half of the color bar. It is only necessary that the color transition be at a velocity which is in the range of velocities where an iso-velocity surface can occur, that is, within the velocities in the acceptance zone which can be used as an iso-velocity surface velocity.

Figure 6:
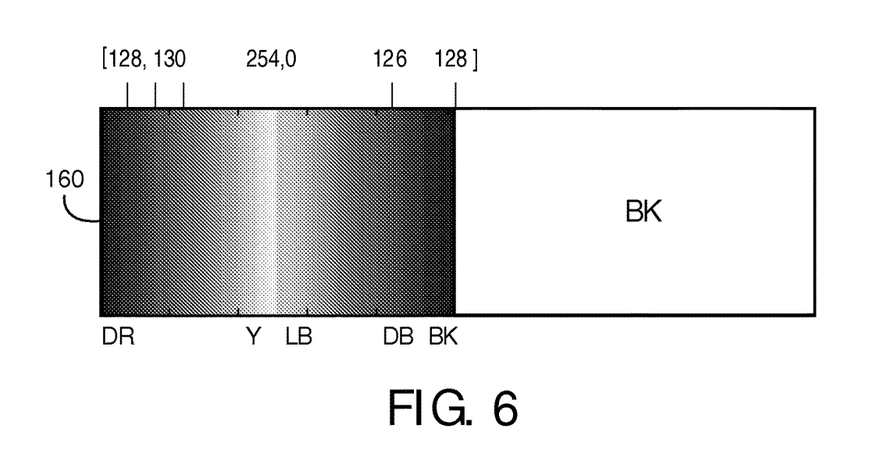
FIG. 6 illustrates a second example of a color bar for a color Doppler image configured in accordance with the present invention.

The example of FIG. 5 employs replication of color spectra with a transition color point both above and below the zero velocity level. A color bar of the present invention can use only half of the color bar area with the other half of the bar set at an arbitrary color such as black, as indicated in FIG. 6. In this implementation the color at the transition color point will change from bright yellow to light blue, or from light blue to bright yellow, depending upon the direction of the jet in relation to the probe placement.

Figure 7:
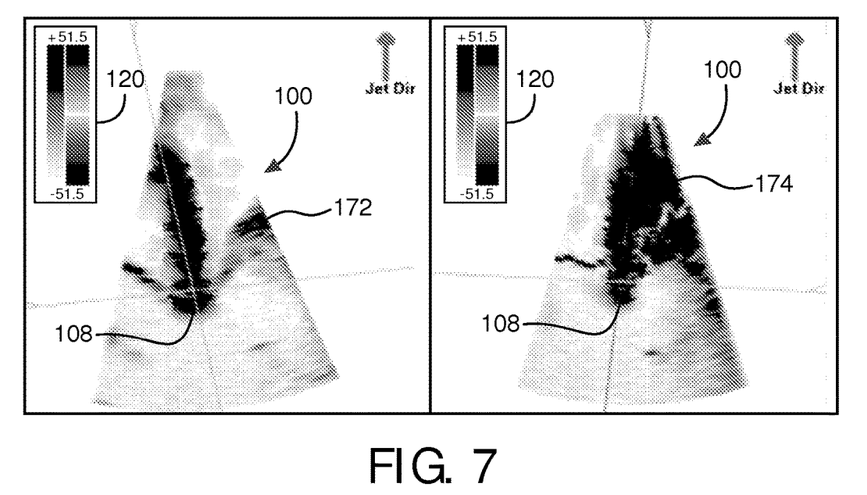
FIG. 7 illustrates biplane color Doppler images of a regurgitant jet using a standard color bar.
Figure 8:
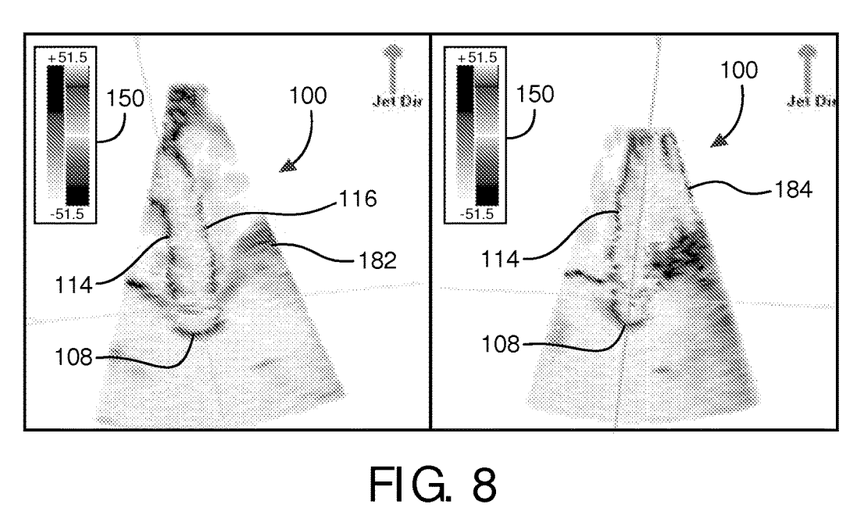
FIG. 8 illustrates biplane color Doppler images of a regurgitant jet using a color bar of the present invention.

FIGS. 7 and 8 are two examples of ultrasound images of mitral regurgitation, one with a standard color bar and the other with a color bar with a distinctive color transition in accordance with the present invention. The left and right images of each drawing figure are two orthogonal biplane images which intersect along a line passing through the leaking valve orifice O. In biplane imaging two image planes are alternately scanned by a 3D imaging probe. Both sets of images are shown with black-white reversal of the images to aid in visualization by eliminating the normal black background of an ultrasound image. This means that the zero velocity color is shown as white in both sets of images and the distinctive color transitions are shown as black in FIG. 8. The upward-pointing arrow in the upper right corner of each ultrasound display indicates an upward direction of the jet as in FIG. 2. In FIG. 7, where the standard color bar 120 is used, the iso-velocity surface 108 is somewhere in the gradual change of colors in the acceptance zone just below the mitral valve plane 100. In both biplane images 172 and 174 an exact, continual iso-velocity surface is difficult to distinguish. But in FIG. 8, the iso-velocity surface is distinguished as a distinct black line 108 (a distinct white line in non-color-reversed normal ultrasound images) in both biplane images 182 and 184. Additionally in this actual imaging example, the boundary of the jet in the atrial chamber above the mitral valve plane 100 is also distinctively marked as seen by distinct black lines 114 and 116 in the two images, enabling the clinician to readily spot the area of and extent of the jet in the atrial chamber.

A distinctive color transition color bar of the present invention can find utility in any colorflow imaging application where it is desirable to identify a line or surface of constant velocity. In some examples, the adjusted shape of the field of the flow velocity may be a parabolic shape, a flattened circular shape, a paraboloid shape, or an oblate spheroid shape.

What is claimed is:

1. A system for producing colorflow images of the velocity of flow or motion, the system comprising:
   an ultrasound probe having a transducer array configured to transmit ultrasonic energy to and receive ultrasonic echoes from a location comprising moving tissue or fluid;
   a processor, responsive to the received ultrasonic echoes, configured to produce Doppler velocity measurements of the tissue or fluid;
   the processor, responsive to the Doppler velocity measurements, being configured to map the Doppler velocity measurements to a plurality of different colors for a color Doppler image;
   the processor, responsive to mapping to the plurality of different colors, being configured to generate a color indicator for display with the color Doppler image by setting, in the color indicator:
      an end velocity level for a first direction corresponding to a first direction-indicating color,
      an end velocity level for a second direction corresponding to a second direction-indicating color,
      a reference level for zero velocity corresponding to a zero-velocity indicating color, and
      a reference level for a velocity of interest corresponding to a distinctive marking color different from the first direction-indicating color, the second direction-indicating color, and the zero-velocity indicating color, such that an iso-velocity surface in the color Doppler image is indicated by the distinctive marking color; and a display device operatively coupled to the processor and configured to display the color Doppler image in conjunction with the color indicator.

2. The system of claim 1, wherein the color indicator further comprises a color bar having a plurality of different colors varying from a first end of the color bar to the zero-velocity indicating color.

3. The system of claim 2, wherein the color bar further comprises a plurality of different colors varying gradually from the zero-velocity indicating color to the distinctive marking color, and a plurality of different colors varying gradually from the distinctive marking color to the first end of the color bar.

4. The system of claim 3, wherein the distinctive marking color corresponds to the velocity of interest in a colorflow image; and further comprising: a user control operable by a user to select the velocity of interest to be identified by the distinctive marking color.

5. The system of claim 2, wherein the color bar further comprises a plurality of different colors varying gradually from the zero-velocity indicating color to the distinctive marking color, and a plurality of different colors varying gradually from the distinctive marking color to a second end of the color bar.

6. The system of claim 5, wherein the distinctive marking color corresponds to the velocity of interest in a colorflow image; and further comprising: a user control operable by a user to select the velocity of interest to be identified by the distinctive marking color.

7. The system of claim 1, wherein the color indicator further comprises a color bar having a plurality of different colors varying from a first end of the color bar to a second end of the color bar with the zero-velocity indicating color located between the two ends of the color bar.

8. The system of claim 7, wherein the distinctive marking color is located between the zero-velocity indicating color and the first end of the color bar; and further comprising: a second distinctive marking color located between the zero-velocity indicating color and the second end of the color bar.

9. The system of claim 1, wherein the colors of the color indicator are further arranged to exhibit the distinctive marking color at a point between the reference level for zero velocity and the end velocity level for the first direction, and wherein aliasing occurs at the end velocity level for the first direction.

10. The system of claim 9, wherein the colors at the end velocity level for the first direction and at the reference level for zero velocity are both the zero-velocity indicating color.

11. The system of claim 9, wherein the distinctive marking color corresponds to a first velocity of interest in a colorflow image; and further comprising: a user control operable by a user and configured to select a second velocity of interest beyond which aliasing occurs.

12. The system of claim 1, wherein the color indicator further comprises a color bar having two ends; wherein the distinctive marking color is located at a first aliasing velocity point between the zero-velocity indicating color and a first end of the color bar; and further comprising: a second distinctive marking color located at a second aliasing velocity point between the zero-velocity indicating color and a second end of the color bar.

13. The system of claim 12, wherein the colors at the first and second ends of the color bar further comprise the zero velocity color.

14. The system of claim 1, wherein the processor is configured to measure mitral regurgitation; and wherein the distinctive marking color is used to identify the iso-velocity surface in the color Doppler image for use in the measurement of mitral regurgitation.

15. The system of claim 14, wherein the distinctive marking color further distinctively indicates a boundary of a regurgitant jet in the color Doppler image.

16. The system of claim 1, wherein the distinctive marking color forms a distinctively bright or dark line in a plurality of gradually changing colors within the color Doppler image to identify the iso-velocity surface.

17. The system of claim 1, wherein the colorflow images are images of a fluid jet, and the iso-velocity surface is displayed such that a boundary of the fluid jet is distinctively marked.

18. The system of claim 1, wherein the colors of the color indicator are further arranged to exhibit the distinctive marking color at a point between the reference level for zero velocity and the end velocity level for the second direction, and wherein aliasing occurs at the end velocity level for the first direction.

19. The system of claim 18, wherein the colors at the end velocity level for the second direction and at the reference level for zero velocity are both the zero-velocity indicating color.

20. The system of claim 18, wherein the distinctive marking color corresponds to a first velocity of interest in a colorflow image; and further comprising: a user control operable by a user and configured to select a second velocity of interest beyond which aliasing occurs.

* * * * *